United States Patent

Conte et al.

[11] Patent Number: 5,626,874
[45] Date of Patent: May 6, 1997

[54] CONTROLLED RELEASE PHARMACEUTICAL TABLET HAVING LENTICULAR FORM

[75] Inventors: Ubaldo Conte, Busto-Arsizio; Aldo La Manna; Lauretta Maggi, both of Pavia, all of Italy

[73] Assignee: Ekita Investments N.V., Curacao, Netherlands Antilles

[21] Appl. No.: 352,072

[22] Filed: Nov. 30, 1994

[30] Foreign Application Priority Data

Nov. 30, 1993 [IT] Italy ................ MI93A2519

[51] Int. Cl.$^6$ .................................................. A61K 9/20
[52] U.S. Cl. .......................... 424/464; 424/467; 424/482
[58] Field of Search ........................... 424/482, 467, 424/464

[56] References Cited

U.S. PATENT DOCUMENTS 4,839,177  6/1989  Colombo et al. ............ 424/482
5,283,065  2/1994  Doyon et al. ................ 424/467

FOREIGN PATENT DOCUMENTS 0432607  6/1991  European Pat. Off. .
0468392  1/1992  European Pat. Off. .
888038   1/1962  United Kingdom .

OTHER PUBLICATIONS

S.H. Yalkowsky. "Techniques of Solubilization".

*Primary Examiner*—Thurman K. Page
*Assistant Examiner*—William E. Benston, Jr.
*Attorney, Agent, or Firm*—Birch, Stewart, Kolasch & Birch, LLP

[57] ABSTRACT

Controlled release pharmaceutical tablet having a lenticular form consisting of three layers of which the central one or core (a) contains the active principle and the two outer layers or barriers (b) and (c) comprise gellable and/or erodible polymeric material, said barrier layers being equal or different among themselves for composition and/or thickness, while the central layer has a limited external annular surface exposed to the dissolution medium, through which the active principle is released.

6 Claims, 3 Drawing Sheets

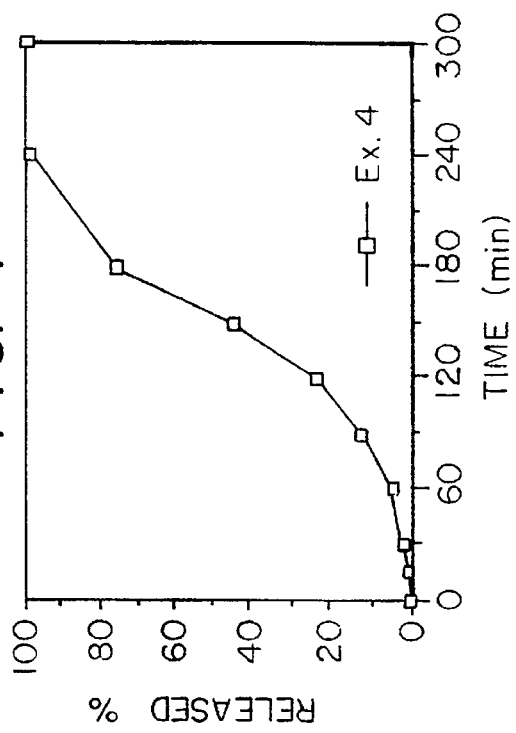
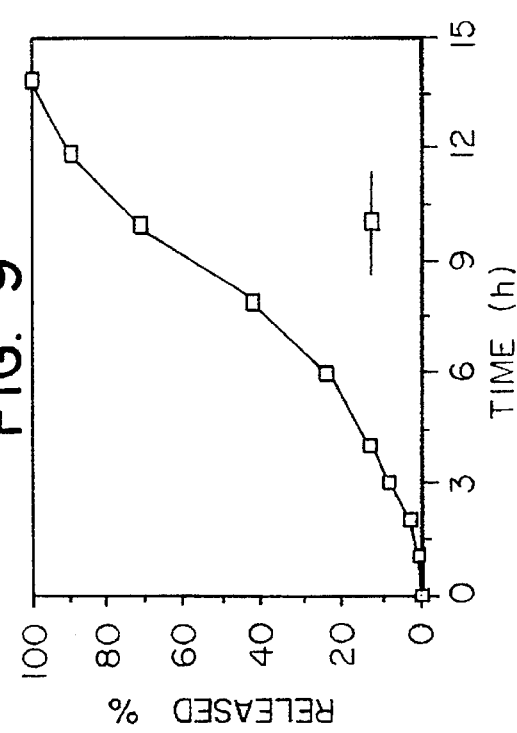
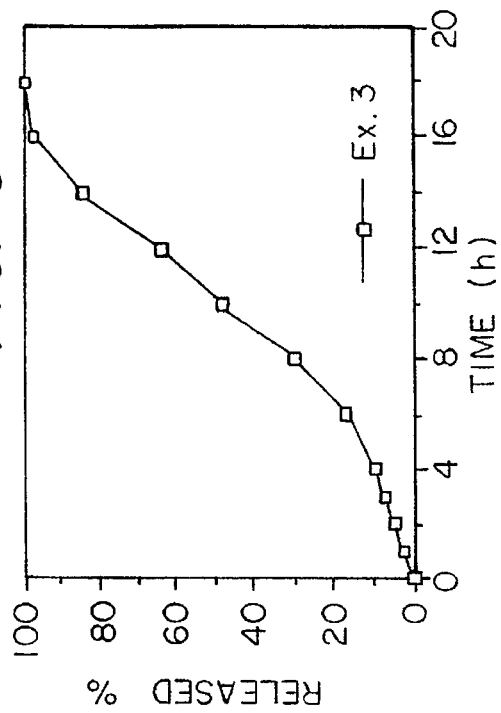
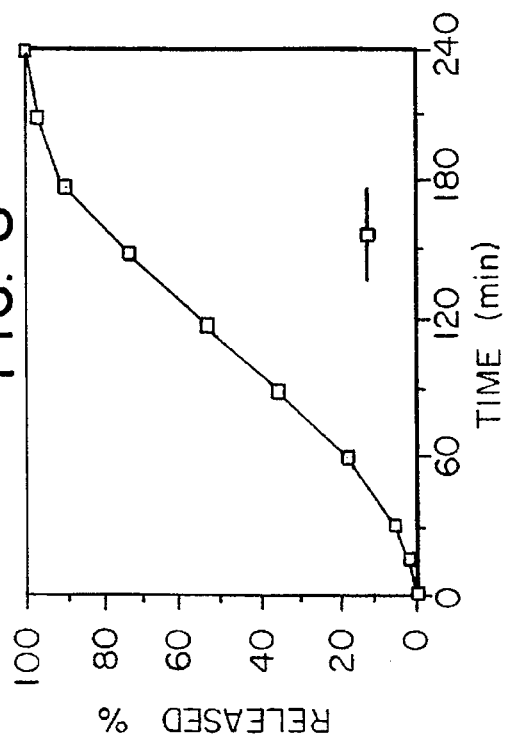

CONTROLLED RELEASE PHARMACEUTICAL TABLET HAVING LENTICULAR FORM

FIELD OF THE INVENTION

The present invention concerns a controlled release tablet, having a lenticular form, consisting of three concentric overposed layers, of which the central one or core (a) contains the active principle and the remaining two outer layers (b) and (c) equal or different among themselves for composition and thickness contain erodible and/or gellable polymeric materials. The new pharmaceutical form has only a limited part of the lateral surface of the core containing the active principle in direct contact with the dissolution medium.

PRIOR ART

In recent years the controlled release pharmaceutical forms and in general the so called therapeutic systems able to release an active substance vehiculed in them for a prolonged period of time and if possible preprogrammable by suitable tests in vitro, have assumed more and more importance.

To reach the controlled release objective, all the systems used in the different application fields need the vehiculation of an high quantity of active substance which, when the system works correctly is gradually released from the system carrying on its activity for a prolonged period of time.

Controlled release compositions are used in agriculture (for insecticides, insect-repellents, slug-killers, fertilizers), in the cosmetic industry (environment and person deodorants, moisturizings) as well as in the pharmaceutical industry.

However, in the pharmaceutical Field the need to have "systems" able to release the active substance, for a prolonged period of time, at a suitable velocity for determining and maintaining high and effective plasmatic levels, is more marked.

As noted above, for all the applications fields, but particularly for the pharmaceutical one, the controlled release systems of the active substance need higher quantities of the active substance to provide a higher expected period of effectiveness, in other words, to provide the active principle at effective therapeutic levels for a longer period of time.

The embodiments carryed out and commercialized until today, for obtaining a prolonged therapeutic covering, or the maintenance of therapeutically effective plasmatic levels of the substance, are numerous.

Examples of such embodiments are the so called "reservoir" systems, the osmotic pumps ("OROS"), and the "PUSH-PULL" systems.

However such systems together with the undoubted advantages also show some undesirable characteristics of structure and function which limit their massive use and in general for long periods of time.

One of the disadvantages associated with such systems is attributable to an accidental and fortuitous deviation from the fixed release program. In fact the difficulty to control the initial release or the accidental abrasion or the breaking of the polymeric membrane, which generally modulates the active substance release, imply the emission of the active substance in high quantities in a very short times, causing a massive adsorption with consequent high hematic levels, sometimes very superior to the tolerability value, and this causes the appearance of toxicity phenomena which in some cases is even serious.

The consequences of such a phenomenon may be reversible or not but in each case they result is extremely dangerous and sometimes lethal.

In general the release of the active principle in a short period of time, better known as "dose dumping", is a particularly critical result for the controlled release forms, which contain high quantities of active principle in comparison to the conventional forms.

The phenomenon of "dose dumping" happens mainly immediately after the therapeutic system administration and is particularly evident in the oral administration of pharmaceutical forms. Even without achievement of irreversible toxic effects, many pharmaceutical forms or therapeutic systems for oral use are commonly characterized by a more or less evident initial phase of "dose dumping", leading to collateral reversible symptoms which are in every case badly suffered by the patient.

Moreover it needs to be pointed out that some therapeutical systems for oral use are obtained by applying a coating on the core. For example the osmotic pump OROS consists of polymeric materials insoluble and not biodegradable in the gastro-intestinal tract and this may imply, as recently occurred, in some patients, phenomena of accumulation in the intestine of the exausted envelopes, which may cause serious consequences and in some cases intestinal occlusions too.

Moreover the quantity of active principle which can be vehiculed in the OROS system is limited because the greatest part of the product is constituted by excipients necessary for the relative activation: for example the administration of 90 mg. of nifedipine implies the use of a very voluminous pharmaceutical form having a diameter of about 14 mm. and weight of about 1 g, which makes its administration almost difficult and problematic, also considering that such a pharmaceutical form cannot be administered in divided or fractionated form for the above reasons.

In literature also other controlled release therapeutic systems which utilize different action mechanism have been described. Among these there are the so called hydrophilic gellable matrices, of great use in therapeutic field, characterized, in general, by a high initial release of the active principle caused by the release of the drug present on the surface of the pharmaceutical form (about 20-40% in the first hour), followed by a more gradual and constant release.

So in the first phase the collateral phenomena linked to the "dose dumping" may occur.

For avoiding the "dose dumping" phenomenon with this kind of hydrophilic matrices a process has been realized to apply an impermeable polymeric film on a part of the matrix systems surface (as it is described for example in the patent U.S. Pat. No. 4,839,177), or, a process of compression and moulding of barrier impermeable to the drug, for a determined range of time (as it is described for example in EP-A-0432607).

A different approach for avoiding the "dose dumping" phenomenon consists in the use of therapeutic forms able to release the active principle vehiculed in them after a determined range of time ("lag time") which may be predetermined on the basis of suitable tests in vitro. Among the utilizable processes, what is described in the U.S. application Ser. No. 08/248,232 is worthy to be cited, which reports a complete coating method of hydrophilic matrices, by compression, using polymeric materials able to allow the release of the drug vehiculated in the hydrophilic matrix only after a well determined range of time, depending on the chemical and physical characteristics of the used polymeric materials and on the thickness of the coating layer. If this pharmaceutical form is perfectly realized, it permits one to obtain correct active principle releases answering to the expectations.

However due to the industrial technology used (dry coating or double compression process) the practical accomplishment of such methodology may show drawbacks and limitations. In fact if the centering of the core containing the drug is not perfectly regulated, the coating material layer determining the delay of the release, does not show homogeneous thickness around the core and this causes a delay not regular and not standardizable with precision of the drug release and so it creates an uncertainty in the administration effectiveness.

SUMMARY OF THE INVENTION

It has been now unexpectedly found that it is possible to prevent the inconveniences of the controlled release compositions of the prior art with the controlled release tablet which is the subject of the present invention.

In particular it has a lenticular form and consists of three superposed and concentric layers of which the central one or core (a) contains the active principle and the two external layers or barrier (b) and (c), limiting the active principle release, comprise gellable and/or erodible polymeric materials.

The barrier layers are equal or different among themselves in terms of composition and/or thickness.

The lateral core (a) surface results the only part at direct contact with the dissolution medium and able to release the active principle. The exposed core surface is about 5–35% of the tablet total surface. Suitably selecting the exposed core surface percentage it is possible to have a zero release or an extremely limited release of the active principle in the first minutes or in the first hours of administration.

With the controlled release tablet according to the present invention it is possible to avoid completely the "dose dumping" phenomenon and it is moreover possible to administer the tablet for the treatment of all the morbid symptoms obeying circadian rithms and for which it is convenient that the active principle release begins after a determined range of time from the administration.

Moreover with the tablet according to the present invention some release profiles may be programmed in relation to the specific therapeutic requirements and of solubility of a certain active principle.

In any case when at least one of the external coatings is eroded and/or solubilized or progressively hydrated, we have the release of the active principle from its matrix with a behaviour programmable by tests in vitro.

BRIEF DESCRIPTION OF THE DRAWINGS

FIGS. 4–9 show dissolution profiles of tested tablets.

DETAILED DESCRIPTION OF THE INVENTION

Figure 1:
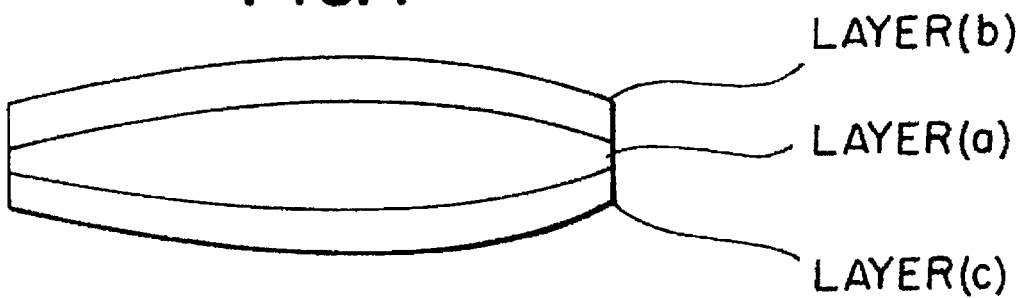
FIGS. 1–3 show three embodiments of the controlled release tablet of the invention.

The characteristics and the advantages of the controlled release tablet object of the present invention will be shown more in detail during the present description.

For the preparation of the tablet according to the present invention active principles with different solubility in water or aqueous media may be used; in the case we use high solubility active principle particular technological processes for slowing the dissolution rate will be used.

Nevertheless active principles which are moderately soluble in aqueous fluids, dependent or not on the pH value of the dissolution medium, and therefore moderately soluble in the gastro-intestinal tract are preferably used. In the case of insufficiently soluble active principles we can utilize particular adjuvants for modifying the solubilization rate as it is for example reported in the volume "Techniques of Solubilization of Drugs" by S. H. Yalkowsky—Ed. M. Dekker, New York 1985 and in EP-A-0468392.

Non steroid antiinflammatory drugs (NSAID) as diclofenac or its pharmacologically acceptable salts and preferably sodium diclofenac, indomethacin, ibuprofen, ketoprofen, diflunisal, piroxicam, naproxen, flurbiprofen, tolmetin or its pharmacologically acceptable salts and preferably sodium tolmetin as well as steroid antiinflammatory drugs as: prednisone, prednisolone, hydrocortisone, desametasone, cortisone, methylprednisolone and their derivatives may be used as active principles in the tablet according to the present invention.

Sleep inductors and tranquillizers as diazepam, nitrazepam, flurazepam, oxazepam, chlordiazepoxide, medazepam, lorazepam; active principles for the anginous attacks prevention as nifedipine, nitrendipine, nicardipine, antistaminic and/or antiasthmatic drugs as efedrine, terfenadine, theophilline, chlorpheniramine or beta-lactamic antibiotics or their derivatives or their pharmacologically acceptable salts as ampicillin, amoxicillin, cefradin, if necessary in association with betalactamase inhibitors as for example the clavulanic acid may be used too.

The core or central layer (a) of the tablet according to the present invention comprises in addition to the active principle polymeric substances able to modulate (to slow and/or to accelerate) the active principle release.

Crosslinked polyvinylpyrrolidone, hydroxypropylmethylcellulose, hydroxypropylcellulose, crosslinked sodium carboxymethylcellulose, carboxymethyl starch, acrylic and methacrylic acid polymers and copolymers, polyesters, polyanhydrides copolymers polymethylvinylether/anhydride, potassium methacrilate-divinylbenzene copolymer, polyvinylalcohols, glucan, scleroglucan, mannan, starchs, starchs derivatives, betacyclodextrins and cyclodextrins derivatives containing linear and/or branched polymeric chains may be used for said purpose, in an amount between 1 and 90% by weight on the total core (a) weight (preferably between 10 and 45%).

For each polymer above described different kinds having different chemical and physical characteristics as molecular weight and consequently the viscosity exist in commerce; therefore they may result soluble in the dissolution medium or tendentially gel or swell according to the fact that the relative molecular weight (or viscosity) is low, medium, or high.

For example about the hydroxypropylmethylcellulose different kinds having different molecular weight (between 1000 and 4.000.000) and different substitution degree inside the polymeric chain may be used for the preparation of the present invention tablet core (a).

Said hydroxypropylmethylcellulose kinds show different characteristics being mostly erodible (soluble) or mostly gellable depending on the viscosity and the substitution degree shown in the polymeric chain.

Therefore the skilled in the field is able to select among polymers with equal molecular structure but different for molecular weight and viscosity, according to how the active principle release from the core must occur.

The core or central layer (a) can eventually contain adjuvant substances of synthetic or natural origin able to further slow the release of the active principle from the core.

The core may contain excipients normally used in the pharmaceutical technology.

For example mannitol, lactose, sorbitol, xilitol and starchs of different origin are used as hydrophilic diluents, when the penetration of water or aqueous fluids in the central layer or core is to be favoured.

Surface-active agents, wetting substances and in general substances helping the penetration of water in the compact may be also used. Excipients as glyceryl monostearate, hydrogenated castor oil, waxes, mono-bi and trisubstituted glycerides are preferably used as hydrophobic diluents, when the penetration of water or aqueous fluids in the core is to be slowed down.

The barrier layers (b) and (c) have the purpose to prevent, for a programmable range of time, the release of the drug contained in the central layer (a).

The barrier layers, as above pointed out, may be equal or different one another both for composition and thickness.

The barrier layers (b) and (c) may contain, in addition to the aforesaid polymers of erodible and/or gellable kind, also adjuvant and plasticizing substances.

The polymers of erodible and/or gellable kind contained in the barrier layer are selected from the group consisting of hydroxypropylmethylcellulose with molecular weight comprised between 1000 and 4.000.000, hydroxypropylcellulose with molecular weight comprised between 2000 and 2.000.000, carboxyvinyl polymers, polyvinylalcohols, glucans, scleroglucans, mannans, xantans, alginic acid and its derivatives, polyanhydrides, polyaminoacids, methylvinyleters/maleic anhydride copolymers, carboxymethylcellulose and its derivatives, ethylcellulose, methylcellulcse, and cellulosic derivatives in general.

Said polymers are generally present in amounts between 5 and 90% and preferably between 50 and 90% by weight with respect to the total weight of the barrier layer.

The adjuvant substances are selected from glyceryl monostearate and semi-synthetic triglycerides derivatives, semi-synthetic glycerides, hydrogenated castor oil, glyceryl palmitostearate, cetyl alcohol, polyvinylpyrrolidone, glycerol, ethylcellulose, methylcellulose, sodiumcarboxymethylcellulose and other natural or synthetic substances well known to the skilled in the field, for example magnesium stearate, stearic acid, talc, sodium benzoate, boric acid, polyoxyethylenglycols and colloidal silica are used.

The adjuvant substances combined to polymeric materials of erodible and/or gellable kind allow to better modulate the resistance time of the barrier layers, making such range variable between 15 minutes and 6-8 hours according to the required therapeutical profile.

The plasticizing substances are selected from: hydrogenated castor oil, cetyl alcohol, cetostearyl alcohol, fatty acids, glycerides and triglycerides as they are or substituted in different ways, polyoxyethylenglicols or their derivatives with different molecular weight usually selected in a range included between 400 and 60,000.

The plasticizing substances have the function to give to the barrier layer the characteristics of compressibility, adherence and cohesion. Moreover the barrier layers (b) and (c) may contain if necessary diluents, binders, lubricants, buffer solutions, antiadherents etc.

Figure 2:
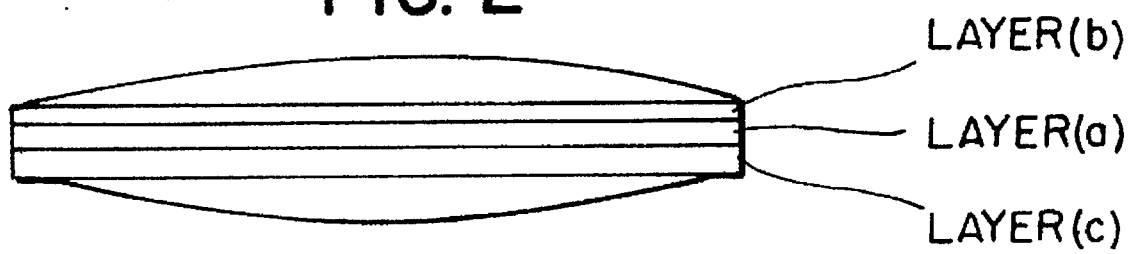
Figure 3:
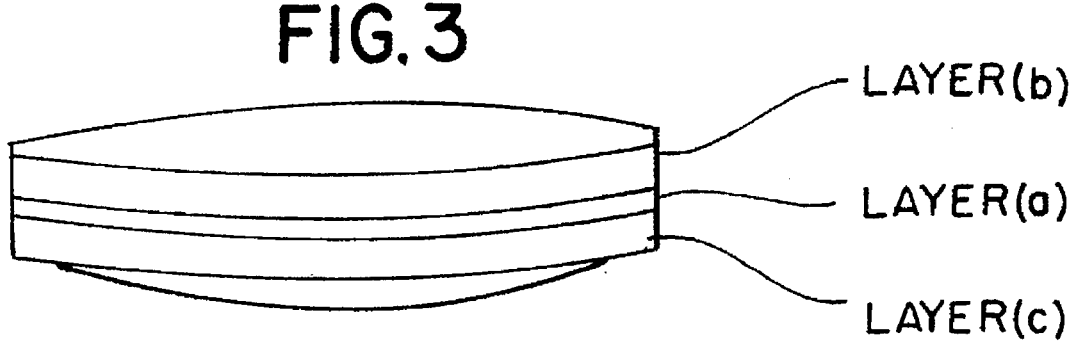

Preferred embodiments of the controlled release three layers lenticular tablet, of which the central layer contains the active principle while the two external barrier layers prevent its release for a pre-arranged period of time, are respectively reported in FIGS. 1, 2 and 3 of the table 1. From the same figures it is evident that, in the lenticular tablet, only a very limited part of the central layer containing the active principle is directly exposed to the dissolution medium.

In fact the Applicant has found that it is possible to avoid the "dose dumping" phenomenon if the surface of the central layer containing the active principle directly exposed to the dissolution medium is comprised between 5 and 35% of the tablet total surface.

This purpose is reached if we give to the tablet the particular lenticular structure according to the present invention, the barrier layers being applied to the core so to leave exposed only a limited portion of the same core lateral surface.

The amount of active substance released in the first administration phase may be programmed regulating the exposed surface and the components constituting the layer (a) matrix, all obviously depending on to the same active principle solubility.

The three layers tablet may be produced using systems of largely consolidated use in the pharmaceutical Field, therefore able to assure a precise and secure realization with extremely limited costs.

On said finished tablets, a polymeric material film will be further applied, which allows a further slowing in the release starting phase. This coating may be soluble in acid medium or permeable to the same or it may be gastroresistant and enterosoluble, in view of allowing the tablet activation only after that the tablet has reached the duodeno-intestinal tract. Said films may be also used for the preparation of tablets specifically projected and assigned to release the active principle only in the last part of the intestinal tract, that is to the colon level.

For obtaining the gastroresistance, polymeric materials as the cellulose acetophthalate, cellulose acetopropionate, cellulose trimellitate, acrylic and methacrylic polymers and copolymers with different molecular weight and with solubility dependent on different pH values may be used. Said materials may be applied on the finished pharmaceutical form (three layers tablet) by the classic film-coating process using solutions in organic solvents or aqueous dispersions and operating by nebulization in basin or in fluidized bed. The tablet submitted to a film-coating process may be further coated with sacchariferous coating by conventional kind techniques, with natural and/or synthetic rubbers as the lacquer gum, sandarac gum and so on, or polymeric materials as cellulose derivatives, for example hydroxypropylmethylcellulose and derivatives.

Some examples of the embodiment of the pharmaceutical tablet according to the present invention are reported for explanatory but not limitative purpose.

EXAMPLE 1

Preparation of a Series of 5000 Tablets as Reported in the FIG. 1, Containing 30 mg of Nifedipine 1-a: Preparation of the Granulate Containing the Active Principle A granulate, according to the procedures later described, is prepared, which is used in the layer (a) of the FIG. 1 preparation. The layer contains 30 mg of the active principle and shows the following unit composition:

| | |
|---|---:|
| Nifedipine (Italian Chemical Industries 3671) | 30,0 mg |
| Sodium carboxymethylcellulose (AcDiSol-FMC) | 90,0 mg |
| Hydroxypropylmethylcellulose (Methocel K 100M Colorcon, Oripington, UK) | 52,0 mg |
| Polyvinylpyrrolidone (Plasdone$^R$ K29-32, Gaf Corp., Wayne, NY, USA) | 20,0 mg |
| Magnesium stearate (C. Erba, Milano, I) | 0,8 mg |
| Colloidal silica (Syloid 244, Grace GmbH,Worms,D) | 0,4 mg |
| Total | 193,2 mg |

The manufacture process consists in the preparation of a granulate by mixing, in a sigma Erweka K5 type mod. (Frankfurt a.M. -D) mixer, the proper amounts of active principle, sodium carboxymethylcellulose and hydroxypropylmethylcellulose; the homogeneous powder mixture is wetted with a 10% (w/v) solution of polyvinylpyrrolidone and the mass homogeneously damp is forced on a 25 mesh (710 μm) grid, obtaining a regular granulate which is dried in a 40°–45° C. air circulation stove. The granulate, dried to a constant weight, is placed in a Turbula T2A mod. (Bachofen-Basel-CH) powder mixer and added with magnesium stearate and colloidal silica and mixed for further 20 minutes.

The lubricated granulate is analyzed for the active principle content and then submitted to the compression stage as forward described.

1-b: Preparation of the Granulate Forming the First Barrier Layer (Gellable)

A requested amount of granulate for obtaining 5000 barrier layers (layer (b) in the FIG. 1) each having the following composition, is prepared:

| | |
|---|---:|
| Hydroxypropylmethylcellulose (Methocel$^R$ K 100M Colorcon, Orpington, UK) | 45,0 mg |
| Hydrogenated castor oil (Cutina HR, Henkel, Dusseldorf D) | 12,0 mg |
| Polyvinylpyrrolidone (Plasdone$^R$ K29-32, Gaf Corp., Wayne, NY, USA) | 2,0 mg |
| Brown lacquer (Eingemann-Veronelli, Milano, I) | 0,1 mg |
| Magnesium stearate (USP grade C. Erba, Milano, I) | 0,6 mg |
| Colloidal silica (Syloid 244, Grace GmbH,Worms,D) | 0,3 mg |
| Total | 60,0 mg |

The manufacture process consists in the preparation of a granulate by mixing, in a sigma Erweka K5 type mod. (Frankfurt a.M. -D) mixer, the proper amounts of hydroxypropylmethylcellulose (Methocel K100M: viscosity 100.000 cps), hydrogenated castor oil and brown lacquer; the homogeneous powder mixture is wetted with a 20% (w/v) solution of polyvinylpyrrolidone and the mass homogeneously damp is forced on a 25 mesh (710 μm) grid, obtaining a regular granulate of clear brown colour which is dried in a 40°–45° C. air circulation stove. The granulate, dried to a constant weight, is placed in a Turbula T2A mod. powder mixer and added with magnesium stearate and colloidal silica and mixed for 20 minutes.

The lubricated granulate is submitted to the compression stage as forward described.

1-c: Preparation of the Granulate Constituting the Second Barrier (Erodible)

A requested amount of granulate for obtaining 5000 barrier layers (layer (c) in the FIG. 1) each having the following composition, is prepared:

| | |
|---|---:|
| Hydroxypropylmethylcellulose (Methocel$^R$ E50 Premium Colorcon, Orpington, UK) | 45,0 mg |
| Hydrogenated castor oil (Cutina HR, Henkel, Dusseldorf D) | 12,0 mg |
| Polyvinylpyrrolidone (Plasdone$^R$ K29-32, Gaf Corp., Wayne, NY, USA) | 2,0 mg |
| Orange lacquer (Eingemann-Veronelli, Milano, I) | 0,1 mg |
| Magnesium stearate (USP grade C. Erba, Milano, I) | 0,6 mg |
| Colloidal silica (Syloid 244, Grace GmbH,Worms,D) | 0,3 mg |
| Total | 60,0 mg |

The manufacture process consists in the preparation of a granulate by mixing, in a sigma Erweka K5 type mod. (Frankfurt a.M. -D) mixer, the proper amounts of hydroxypropylmethylcellulose (Methocel 50 E: viscosity 50 cps), hydrogenated castor oil and orange lacquer; the homogeneous powder mixture is wetted with a 20% (w/v) alcoholic solution of polyvinylpyrrolidone and the mass homogeneously damp is forced on a 25 mesh (710 μm) grid, obtaining a regular granulate of orange colour which is dried in a 40°–45° C. air circulation stove. The granulate, dried to a constant weight, is placed in a Turbula T2A mod. powder mixer and added with magnesium stearate and colloidal silica and mixed for 20 minutes.

The lubricated granulate is submitted to the compression stage as forward described.

1-d: Preparation of the Three Layers Systems (by Compression)

The granulates obtained according to what described and according to patterns well known to the skilled in the field are loaded in the three loading hoppers of a rotating press suitable to produce three layers tablets (ex. Manesty Layer—Press, Liverpool UK).

In particular in the first hopper the granulate described at point 1-b is loaded; in the second hopper the granulate described at point 1-a is loaded, while in the third hopper the granulate described at point 1-c is loaded.

The press machine ms equipped with circular convex punchs of 10 mm diameter and bending radius R=12 mm.

The machine is adjusted for producing three layers systems constituted by a first share of 60 mg of slow hydration barrier granulate (gellable barrier), a second layer of 193.2 mg containing the active principle (equivalent to 30 mg of nifedipine) and a third layer of 60 mg of erodible barrier (amounts of used barriers being necessary to obtain the thickness of about 1.0 mm).

1-e: Comparison Tablets

To estimate the effect of the two barriers applied to the central core, working as formerly described a tablets series (cores without barriers) using the formulation described in 1-a, obtaining convex tablets of 10 mm diameter (R=12 mm) and 193,2 mg weight convex tablets containing 30 mg of active principle, and a series of tablets with only one barrier and precisely using the granulates described in 1-a (granulate with active principle) and 1-b (gellable barrier) obtaining convex tablets of 10 mm diameter (R=12 mm) and 253,2 weight (i.e. with 193,2 mg of granulate equivalent to 30 mg of active principle and 60 mg of the barrier described in 1-b) have been prepared.

1-f: Dissolution Test

To estimate the releasing characteristics of the finished systems the equipment 2 is used, (paddle USP XXII) adapted to a 5 l capacity container for maintaining the "sink conditions" working at 100 r.p.m. and using 5 l of deionized water at 37 ° C. as dissolution fluid.

The active principle release is followed by 237 nm U.V. spectrophotometric determination using an automatic system of sampling and reading (Spectracomp 602 by Advanced Products—Milan).

Figure 4:
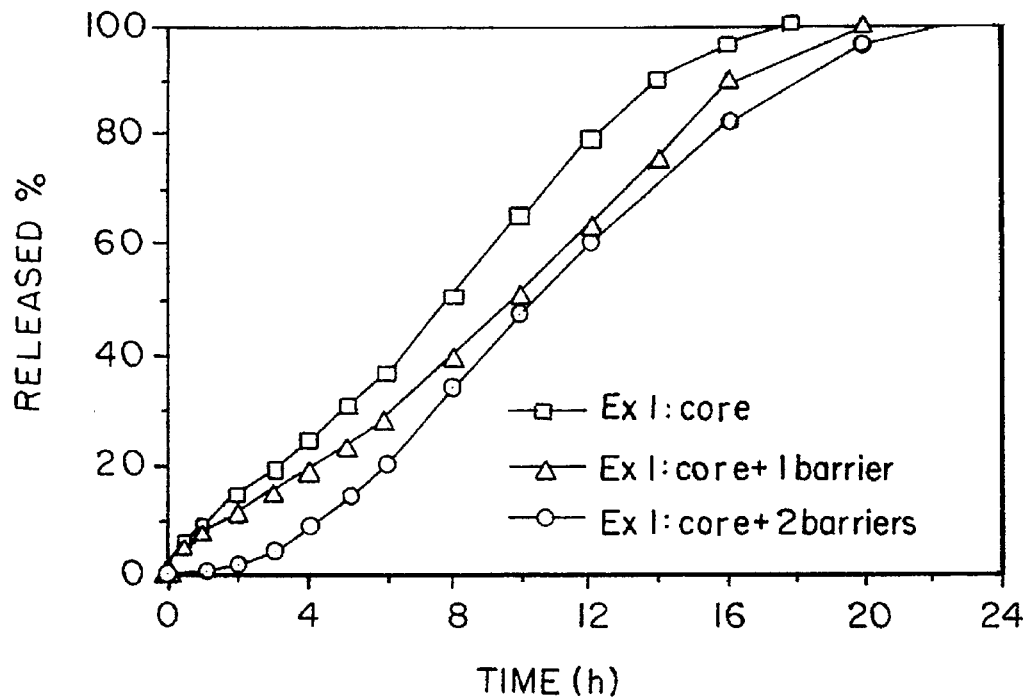

The results of the effected tests are reported in the table I and the dissolution profiles in the FIG. 4.

TABLE I

| Time (h) | Core released % | Core + one barrier released % | Core + two barriers released % |
|---|---|---|---|
| 0,5 | 6,9 | 5,9 | 0,0 |
| 1 | 10,1 | 8,3 | 0,6 |
| 2 | 14,8 | 12,0 | 2,3 |
| 3 | 19,2 | 15,4 | 4,7 |
| 4 | 24,9 | 19,6 | 8,9 |
| 5 | 30,8 | 23,8 | 14,0 |
| 6 | 37,0 | 28,6 | 20,1 |
| 8 | 50,5 | 39,4 | 33,9 |
| 10 | 65,3 | 51,0 | 47,7 |
| 12 | 78,9 | 63,4 | 60,3 |
| 16 | 96,2 | 88,8 | 81,3 |
| 20 | 99,8 | 98,6 | 96,2 |

It is possible to point out how the drug release from the two barriers tablet according to the present invention occurs after a starting range of 3 hours during which the active principle is not practically released or anyway during which the release is extremely slowed.

Then a second phase occurs very different from the former, during which the drug is released at controlled rate of about 6%/h while using just the core without any barrier or the system with one only gellable barrier, the active principle release begins immediately. Such behaviour answers completely to the invention aims.

Total area 266.6 mm$^2$; exposed area 54,3 mm$^2$; exposed area 20,3%.

EXAMPLE 2

Preparation of a Series of 5000 Tablets as Reported in the FIG. 1, Containing as Active Principle 30 mg of Nifedipine with Different Amount of Erodible Barrier 2-a: Preparation of the Granulate Containing the Active Principle A granulate according to the procedures described in the former example at the point 1-a which is used in the preparation of the layer (a) of the FIG. 1 is prepared.

2-b: Preparation of the Granulate Forming the First Barrier Layer

An amount of granulate required for obtaining 5000 barrier layers (layer (b) in the FIG. 1) is prepared as described in the former example at the point 1-b.

2-c: Preparation of the Granulate Constituting the Second Barrier Layer

An amount of granulate required for obtaining 5000 barrier layers (layer (c) in the FIG. 1) each having the following composition is prepared:

| | |
|---|---|
| Hydroxypropylmethylcellulose (Methocel$^R$ E 50 Premium Colorcon, Orpington, UK) | 90 mg |
| Hydrogenated castor oil (Cutina HR, Henkel, Dusseldorf D) | 24,0 mg |
| Polyvinylpyrrolidone (Plasdone$^R$ K29-32, Gaf Corp., Wayne, NY, USA) | 4,1 mg |
| Orange lacquer (Eingemann-Veronelli, Milano, I) | 0,1 mg |
| Magnesium stearate (USP grade C. Erba, Milano, I) | 1,2 mg |
| Colloidal silica (Syloid 244, Grace GmbH,Worms,D) | 0,6 mg |
| Total | 120,0 mg |

The manufacture process consists in the preparation of a granulate by mixing in a sigma Erweka K5 type mod. (Frankfurt am. M., D) mixer, the proper amounts of hydroxypropylmethylcellulose (Methocel 50 E: apparent viscosity 50 cps), hydrogenated castor oil and orange lacquer; the homogeneous powder mixture is wetted with a 20% (w/v) solution of polyvinylpyrrolidone and the mass homogeneously damp is Forced on a 25 mesh (710 µm) grid, obtaining a regular granulate of light orange colour which is dried in a 40°–45° C. air circulation stove. The granulate, dried to a constant weight, is placed in a Turbula T2A mod. powder mixer and added with magnesium stearate and colloidal silica and mixed for 20 minutes.

The lubricated granulate is submitted to the compression stage as forward described.

2-d: Preparation of the Three Layers Systems (by Compression)

The granulates obtained according to what formerly reported are loaded in the three loading hoppers of a rotating press suitable to produce Three layers tablets (ex. Manesty Layer—Press, Liverpool UK).

In particular in the first hopper the granulate described at the point 2-b is loaded; while in the second hopper the granulate according to what is described at the former point 2-a is loaded and in the third hopper the granulate described at the point 2-c is loaded.

The pressing machine is equipped with circular convex punchs of 10 mm diameter and R=12 mm.

The machine is adjusted for producing three layers systems constituted by a first share of 60 mg slow hydration barrier granulate (gellable barrier), a second layer of 193.2 mg containing the active principle (equivalent to 30 mg of nifedipine) and a third layer of 120 mg of erodible barrier (the amount of barrier used for this last layer being necessary to obtain the thickness of about 2,0 mm).

Working as formerly described, three layers tablets of 343,2 mg average weight each containing 30 mg of active principle are obtained.

2-e: Dissolution Test

Figure 5:
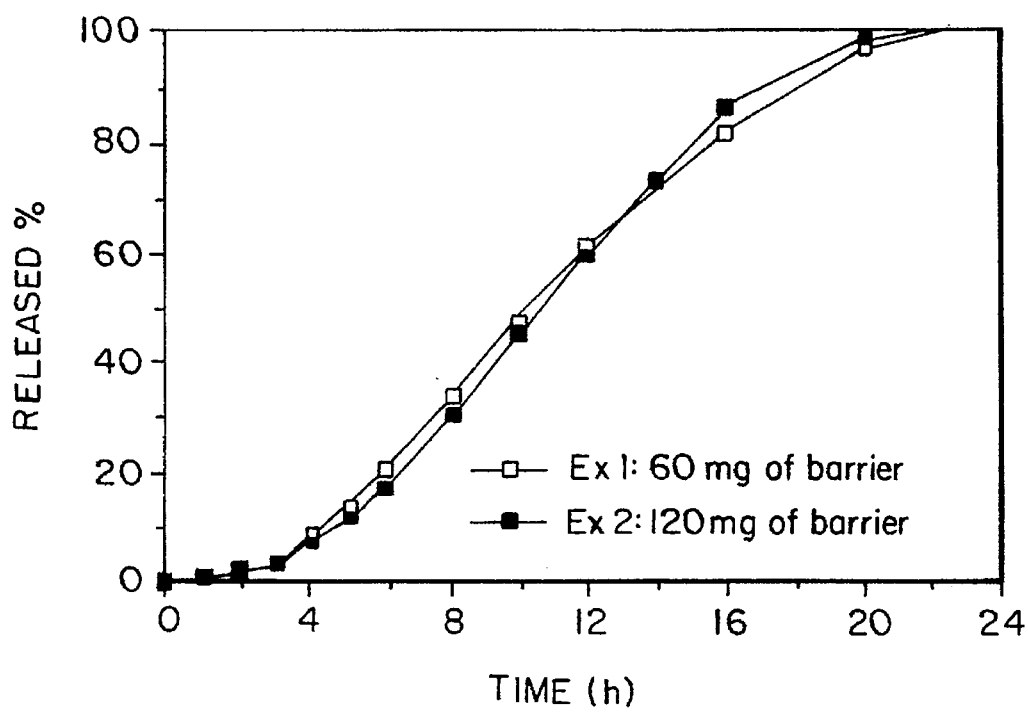

To estimate the releasing characteristics of the finished systems the equipment and the methods described in the former example at the point 1-e are used. The results of the effected tests are reported in the table II and the dissolution profiles in the FIG. 5.

TABLE II

| Time (h) | % released from the system with 120 mg of barrier ex. 2 | % released from the system with 60 mg of barrier ex. 1 |
|---|---|---|
| 1 | 0,7 | 0,6 |
| 2 | 2,0 | 2,3 |
| 3 | 4,2 | 4,7 |
| 4 | 8,0 | 8,9 |
| 5 | 12,0 | 14,0 |
| 6 | 17,1 | 20,1 |
| 8 | 30,1 | 33,9 |

TABLE II-continued

| Time (h) | % released from the system with 120 mg of barrier ex. 2 | % released from the system with 60 mg of barrier ex. 1 |
|---|---|---|
| 10 | 45,1 | 47,7 |
| 12 | 59,3 | 60,3 |
| 16 | 85,7 | 81,3 |
| 20 | 98,2 | 96,2 |
| 24 | 100,3 | 100,3 |

It is possible to point out that the prepared system is actived only after a range of about 3 hours during which the drug is practically not released or anyway the release is extremely slowed, and a second phase, very different from the former, during which the drug is released at controlled Fate of about 7%/h.

Such behaviour completely answers to the invention aims and the result confirms that the erodible barrier, applied on a base of the tablet is eroded and/or solubilized in a predeterminable range of time, independently from the applied amount, leaving free for the active principle release a well determined surface of the core on which the barrier layers are applied.

Total area 287,3 mm$^2$; exposed area 53,9 mm$^2$; exposed area 18,7%.

EXAMPLE 3

Preparation of a Series of 5000 Tablets as Reported in the FIG. 1, Containing 60 mg of Nicardipine HCl as Active Principle 3-a: Preparation of the Granulate Containing the Active Principle A granulate is prepared according to the procedures forward described which is used in the preparation of the layer (a) of the FIG. 1. The layer contains 60 mg of active principle and shows the following unit composition:

| | |
|---|---|
| Nicardipine HCl (Medioplast B. 5/91) | 60,0 mg |
| Mannitol (C. Erba, Milano, I) | 120,0 mg |
| Hydroxypropylmethylcellulose (Methocel K 15 M, Colorcon, Orpington, UK) | 30,0 mg |
| Polyvinylpyrrolidone (Plasdone$^R$ K29-32 Gaf Corp. Wayne, NY, USA) | 14,0 mg |
| Magnesium stearate (C. Erba, Milano, I) | 4,0 mg |
| Colloidal silica (Syloid 244, Grace GmbH,Worms,D) | 2,0 mg |
| Total | 240 mg |

The manufacture process consists in the preparation of a granulate by mixing, in a sigma Erweka K5 type mod. (Frankfurt a.M. -D) mixer, the proper amounts of active principle, mannitol and hydroxypropylmethylcellulose; the homogeneous powder mixture is wetted with a 10% (w/v) alcoholic solution of polyvinylpyrrolidone and the mass homogeneously damp is forced on a 25 mesh (710 μm) grid obtaining a regular granulate which is dried in a 40°45° C. air circulation stove. The granulate, dried to a constant weight, is placed in a Turbula T2A mod. (Bachofen-Basel-CH) powder mixer, added with magnesium stearate and colloidal silica and mixed for 20 minutes.

The granulate lubricated and analyzed for the active principle content, is submitted to the compression stage as forward described.

3-b: Preparation of the Granulate Constituting Two Equal Barrier Layers (Erodible)

An amount of granulate necessary for obtaining 10.000 barrier layers, each having the following composition is prepared:

| | |
|---|---|
| Hydroxypropylmethylcellulose (Methocel$^R$ E 5 Premium Colorcon, Orpington, UK) | 45,0 mg |
| Hydrogenated castor oil (Cutina HR, Henkel, Dusseldorf D) | 12,0 mg |
| Polyvinylpyrrolidone (Plasdone$^R$ K29-32, Gaf Corp., Wayne, NY, USA) | 2,0 mg |
| Orange lacquer (Eingemann-Veronelli, Milano, I) | 0,1 mg |
| Magnesium stearate (USP grade C. Erba, Milano, I) | 0,6 mg |
| Colloidal silica (Syloid 244, Grace GmbH,Worms,D) | 0,3 mg |
| Total | 60,0 mg |

The manufacture process consists in the preparation of a granulate by mixing, in a sigma Erweka K5 type mod. (Frankfurt a.M. -D) mixer, the proper amounts of hydroxypropylmethylcellulose (Methocel E5: apparent viscosity 5 cps), hydrogenated castor oil and orange lacquer; the homogeneous powder mixture is wetted with a 20% (w/v) alcoholic solution of polyvinylpyrrolidone and the mass homogeneously damp is forced on a 25 mesh (710 μm) grid obtaining a regular granulate of light orange colour which is dried in a 40°–45° C. air circulation stove. The granulate, dried to a constant weight, is placed in a Turbula T2A mod. powder mixer and added with magnesium stearate and colloidal silica and mixed for 20 minutes.

The lubricated granulate is submitted to the compression stage as forward described.

3-c: Preparation of the Three Layers Systems (by Compression)

The granulates obtained according to what is formerly reported and according to the patterns well known to all the skilled in the field, are loaded in the three loading hoppers of a rotating press suitable to produce three layers tablets (ex. Manesty Layer—Press, Liverpool UK). In particular in the first and in the third hoppers the granulate described at the point 3-b is loaded; while in the second hopper the granulate according to what is described in the former point 3-a is loaded.

The pressing machine is equipped with circular convex punchs of 10 mm diameter and R=12 mm.

The machine is adjusted for producing three layers systems consisting of a first share of 60 mg of erodible barrier granulate, a second layer of 240 mg containing the active principle (equivalent to 60 mg of nicardipine HCl) and a third layer of 60 mg of erodible barrier.

Working as formerly described, three layers tablets of 360 mg average weight each containing 60 mg of active principle are obtained.

3-d: Dissolution Test

To estimate the releasing characteristics of the finished systems the equipment 2 (paddle USP XXII) at 100 r.p.m. is used and as dissolution fluid 1 liter of simulated gastric fluid pH=1,2 (according to USP XXII, without enzymes) at 37° C. is used. The active principle release is followed by 240 nm U.V. spectrophotometric determination using an automatic system of sampling and reading (Spectracomp 602 by Advanced Products—Milano).

The results of the effected tests are reported in the table III.

TABLE III

| Time (h) | % released |
|---|---|
| 1 | 2,3 |
| 2 | 4,8 |
| 3 | 6,8 |
| 4 | 9,4 |
| 5 | 16,6 |
| 6 | 30,0 |
| 8 | 48,0 |
| 10 | 64,1 |
| 12 | 84,3 |
| 16 | 97,6 |
| 18 | 99,8 |

It is possible to point out that from the prepared systems it is obtained a range during which the drug release results extremely slowed, for at least ¾ hours, and a second phase, clearly different from the former, during which the drug is released at controlled rate of 8–10%/h.

Such behaviour completely answers to the invention aims.

Total area 253,6 mm$^2$; exposed area 62,7 mm$^2$; exposed area 24,7%.

EXAMPLE 4

Preparation of a Series of 5000 Tablets as Reported in the FIG. 1, Containing 500 mg of Diflunisal as Active Principle 4-a: Preparation of the Granulate Containing the Active Principle A granulate, according to the procedures further described, which is used in the preparation of the layer (a) of the FIG. 1 is prepared. The layer contains 500 mg of active principle and shows the following unit composition:

| | |
|---|---|
| Diflunisal (Morson's Lot 008H152) | 500,0 mg |
| Mannitol (C. Erba, Milano, I) | 100,0 mg |
| Hydroxypropylmethylcellulose (methocel K 15 M, Colorcon, Orpington, UK) | 120,0 mg |
| Polyvinylpyrrolidone (Plasdone$^R$ K29-32,ISP USP) | 30,0 mg |
| Magnesium stearate (C. Erba, Milano, I) | 8,0 mg |
| Colloidal silica (Syloid 244, Grace GmbH,Worms,D) | 2,0 mg |
| Total | 760 mg |

The manufacture process consists in the preparation of a granulate by mixing, in a sigma Erweka K5 type mod. (Frankfurt a.M. -D) mixer, the proper amounts of active principle, mannitol and hydroxypropylmethylcellulose: the homogeneous powder mixture is wetted with a 10% (w/v) alcoholic solution of polyvinylpyrrolidone and the mass homogeneously damp is forced on a 25 mesh (710 µm) grid, obtaining a regular granulate, which is dried in a 40°–45° C. air circulation stove. The granulate, dried to a constant weight, is placed in a Turbula T2A mod. (Bachofen-Basel-CH) powder mixer, added with magnesium stearate and colloidal silica and mixed for further 20 minutes.

The granulate lubricated and analyzed For the active principle content is submitted to the compression stage as forward described.

4-b: Preparation of the Granulate Constituting Two Equal Barrier Layers

An amount of granulate necessary for obtaining 10.000 barrier layers (layers (b) and (c) of the FIG. 1), each having the Following composition is prepared:

| | |
|---|---|
| Hydroxypropylmethylcellulose (Methocel$^R$ K 100M Colorcon, Orpington, UK) | 82,5 mg |
| Hydrogenated castor oil (Cutina HR, Henkel, Dusseldorf, D) | 22,0 mg |
| Polyvinylpyrrolidone (Plasdone$^R$ K29-32, Gaf Corp., Wayne, NY, USA) | 3,8 mg |
| Orange lacquer (Eingemann-Veronelli, Milano, I) | 0,1 mg |
| Magnesium stearate (C. Erba, Milano, I) | 1,1 mg |
| Colloidal silica (Syloid 244, Grace GmbH,Worms,D) | 0,5 mg |
| Total | 110,0 mg |

The manufacture process consists in the preparation of a granulate by mixing, in a sigma Erweka K5 type mod. (Frankfurt a.M. -D) mixer, the proper amounts of hydroxypropylmethylcellulose (Methocel K 100M: viscosity 100.000 cps), hydrogenated castor oil and orange lacquer; the homogeneous powder mixture is wetted with a 20% (w/v) alcoholic solution of polyvinylpyrrolidone and the mass homogenously damp is forced on a 25 mesh (710 µm) grid, obtaining a regular granulate, of light orange colour which is dried in a 40°–45° C. air circulation stove. The granulate, dried to a constant weight, is placed in a Turbula T2A mod. powder mixer and added with magnesium stearate and colloidal silica and mixed for 20 minutes.

The lubricated granulate is submitted to the compression stage as forward described.

4-c: Preparation of the Three Layers Systems (by Compression)

The granulates obtained according to what is Formerly reported and according to the patterns well known to all the skilled in the Field, are loaded in the three loading hoppers of a rotating press suitable to produce three layers tablets (ex. Manesty Layer—Press, Liverpool UK). in the first and in the third hoppers the granulate described at the point 4-b is loaded, while in the second hopper the granulate according with what is described at the former point 4-a is loaded.

The pressing machine is equipped with oval convex punchs of dimensions 9×19 mm.

The machine is adjusted for producing three layers systems constituted by a first share of 110 mg of slow hydration barrier granulate, a second layer of 760 mg containing the active principle (equivalent to 500 mg of diflunisal) and a third layer of 110 mg of slow hydration barrier.

Working as formerly described, three layers tablets of 980 mg average weight each containing 500 mg of active principle are obtained.

4-d: Dissolution Test

To estimate the releasing characteristics of the finished systems the equipment 2 is used (paddle USP XXII) at 100 r.p.m. is used, using as dissolution fluid 1 liter of simulated intestinal fluid pH=7,5 (according to USP XXII, without enzymes) at 37° C. The active principle release is measured by 360 nm U.V. spectrophotometric determination using an automatic system of sampling and reading (Spectracomp 602 by Advanced Product, Milano).

The results of the effected tests are reported in the table IV.

TABLE IV

| Time (min) | % released |
|---|---|
| 15 | 0,9 |
| 30 | 1,7 |
| 60 | 4,8 |
| 90 | 12,9 |
| 120 | 24,1 |
| 150 | 44,4 |
| 180 | 76,4 |
| 240 | 99,0 |
| 300 | 100,0 |

It is possible to point out that from the prepared systems it is obtained a range during which the drug is practically not released for at least 1 hour, and a second phase, clearly different from the former, during which the drug is released at controlled rate in about 4 hours. Such behaviour completely answers to the invention aims.

Total area 483,2 mm$^2$; exposed area 154,0 mm$^2$; exposed area 31,9%.

EXAMLE 5

Preparation of a Series of 5000 Tablets as Reported in the FIG. 1, Containing 500 mg of Diflunisal as Active Principle 5-a: Preparation of the Granulate Containing the Active Principle A granulate according to the procedures described in the example 4-a is prepared.

5-b: Preparation of the Granulate Forming the Two Equal Barrier Layers

An amount of granulate required for obtaining 10,000 barrier layers each having the following composition is prepared:

| | |
|---|---|
| Hydroxypropylmethylcellulose (Methocel$^R$ E5 Premium Colorcon, Orpington, UK) | 82,5 mg |
| Hydrogenated castor oil (Cutina HR, Henkel, Dusseldorf, D) | 22,0 mg |
| Polyvinylpyrrolidone (Plasdone$^R$ K29-32, Gaf Corp., Wayne, NY, USA) | 3,8 mg |
| Green lacquer (Eingemann-Veronelli, Milano, I) | 0,1 mg |
| Magnesium stearate (USP grade C. Erba, Milano, I) | 1,1 mg |
| Colloidal silica (Syloid 244, Grace GmbH,Worms,D) | 0,5 mg |
| Total | 110,0 mg |

The manufacture process consists in the preparation of a granulate by mixing, in a sigma Erweka K5 type mod. (Frankfurt a.M., D) mixer, the proper amounts of hydroxypropylmethylcellulose (Methocel E5, viscosity 5 cps), hydrogenated castor oil and green lacquer; the homogeneous powder mixture is wetted with a 20% (w/v) alcoholic solution of polyvinylpyrrolidone and the mass homogeneously damp is forced on a 25 mesh (710 µm) grid, obtaining a regular granulate of light green colour which is dried in a 40°–45° C. air circulation stove. The granulate, dried to a constant weight, is placed in a Turbula T2A mod. powder mixer and added with magnesium stearate and colloidal silica and mixed for 20 minutes.

The lubricated granulate is submitted to the compression stage as forward described.

5-c: Preparation of the Three Layers Systems (by Compression)

The granulates obtained according to what is formerly reported and according to the patterns well known to all the skilled in the field, are loaded in the three loading hoppers of a rotating press suitable to produce three layers tablets (ex. Manesty Layer—Press, Liverpool UK). In particular in the first and in the Third hoppers the granulate described at the point 5-b is loaded, while in the second hopper the granulate according to what is described at the former point 5-a is loaded.

The pressing machine is equipped with oval convex punchs of dimensions 9×19 mm.

The machine is adjusted for producing three layers systems constituted by a first share of 110 mg of erodible barrier granulate, a second layer of 760 mg containing the active principle (equivalent to 500 mg of diflunisal) and a third layer of 110 mg of the same erodible barrier.

Working as formerly described, three layers tablets of 980 mg average weight each containing 500 mg of active principle are obtained.

5-d: Dissolution Test

To estimate the releasing characteristics of the finished systems the equipment and the methods described in the example 4 at the point 4-d, are used.

The results of the effected tests are reported in the table V.

TABLE V

| Time (min) | % released |
|---|---|
| 15 | 1,7 |
| 30 | 5,7 |
| 60 | 17,8 |
| 90 | 34,9 |
| 120 | 52,8 |
| 150 | 72,9 |
| 180 | 90,8 |
| 240 | 100,8 |

It is possible to point out that from the prepared systems it is obtained a range of 30 minutes during which the drug release results extremely slowed and a second phase, clearly different from the former, during which the drug is released at controlled rate in about 4 hours. Such behaviour completely answers to the invention aims.

Total area 480,2 mm$^2$; exposed area 151,0 mm$^2$; exposed area 32,0%.

EXAMPLE 6

Preparation of a Series of 5000 Tablets as Reported in the FIG. 1, containing 100 mg of Ketoprofene as Active Principle 6-a: Preparation of the Granulate Containing the Active Principle A granulate, according to the procedures forward described, which is used in the preparation of the layer (a) of the FIG. 1, is prepared. The layer contains 100 mg of active principle and shows the following unit composition:

| | |
|---|---|
| Ketoprofene (Sims - batch n. 16577) | 100,0 mg |
| Mannitol (C. Erba, Milano, I) | 40,0 mg |
| Hydroxypropylmethylcellulose (methocel K 4 M, Colorcon, Orpington, UK) | 75,0 mg |
| Polyvinylpyrrolidone (USP grade) | 15,0 mg |
| Magnesium stearate (C. Erba, Milano, I) | 1,0 mg |
| Colloidal silica (Syloid 244, Grace GmbH,Worms,D) | 0,5 mg |
| Total | 231,5 mg |

The manufacture process consists in the preparation of a granulate by mixing, in a sigma Erweka K5 type mod. (Frankfurt a.M. -D) mixer, the proper amounts of active principle, mannitol and hydroxypropylmethylcellulose; the homogeneous powder mixture is wetted with a 10% (w/v) alcoholic solution of polyvinylpyrrolidone and the mass homogeneously damp is forced on a 25 mesh (710 µm) grid, obtaining a regular granulate, which is dried in a 40°–45° C. air circulation stove. The granulate, dried to a constant weight, is placed in a Turbula T2A mod. (Bachofen-Basel-CH) powder mixer.

Magnesium stearate and colloidal silica are then added to the mixture and mixed for further 20 minutes.

The granulate lubricated and analized for the active principle content is submitted to the compression stage as forward described.

6-b: Preparation of the Granulate Forming the First Slow Hydration Barrier Layer An amount of granulate required for obtaining 5.000 barrier layers (layer (b) of the FIG. 1) each having the following composition is prepared:

| | |
|---|---|
| Hydroxypropylmethylcellulose (Methocel$^R$ K 4M Colorcon, Orpington, UK) | 40,5 mg |
| Mannitol (C. Erba, Milano, I) | 40,5 mg |
| Polyvinylpyrrolidone (Plasdone$^R$ K29-32, Gaf Corp., Wayne, NY, USA) | 7,6 mg |
| Red lacquer (Eingemann-Veronelli, Milano, I) | 0,1 mg |
| Magnesium stearate (USP grade C. Erba, Milano, I) | 0,9 mg |
| Colloidal silica (Syloid 244, Grace GmbH,Worms,D) | 0,4 mg |
| Total | 90,0 mg |

The manufacture process consists in the preparation of a granulate by mixing, in a sigma Erweka K5 type mod. (Frankfurt a.M., D) mixer, the proper amounts of hydroxypropylmethylcellulose (Methocel K 4M: viscosity 4000 cps), mannitol and red lacquer; the homogeneous powder mixture is wetted with a 20% (w/v) alcoholic solution of polyvinylpyrrolidone and the mass homogeneously damp is forced on a 25 mesh (710 µm) grid, obtaining a regular granulate, of pink color which is dried in a 40°–45° C. air circulation stove.

The granulate, dried to a constant weight, is placed in a Turbula T2A mod. powder mixer and added with magnesium stearate and colloidal silica and mixed for 20 minutes.

The lubricated granulate is submitted to the compression stage as forward described.

6-c: Preparation of the Granulate Forming the Second Barrier Layer

An amount of granulate required for obtaining 5.000 barrier layers (layer (c) of the FIG. 1) each having the following composition is prepared:

| | |
|---|---|
| Hydroxypropylmethylcellulose (Methocel$^R$ E50 Premium Colorcon. Orpington, UK) | 67,5 mg |
| Hydrogenated castor oil (Cutina HR, Henkel, Dusseldorf, D) | 18,0 mg |
| Polyvinylpyrrolidone (Plasdone$^R$ K29-32, Gaf Corp., Wayne, NY, USA) | 3,1 mg |
| Orange lacquer (Eingemann-Veronelli, Milano, I) | 0,1 mg |
| Magnesium stearate (USP grade C. Erba, Milano, I) | 0,9 mg |
| Colloidal silica (Syloid 244, Grace GmbH,Worms,D) | 0,5 mg |
| Total | 90,0 mg |

The manufacture process consists in the preparation of a granulate by mixing, in a sigma Erweka K5 type mod. (Frankfurt a. M., D) mixer, the proper amounts of hydroxypropylmethylcellulose (Methocel 50E: apparent viscosity 50 cps), hydrogenated castor oil and orange lacquer; the homogeneous powder mixture is wetted with a 20% (w/v) alcoholic solution of polyvinylpyrrolidone and the mass homogeneously damp is forced on a 25 mesh (710 µm) grid, obtaining a regular granulate, of clear orange color which is dried in a 40°–45° C. air circulation stove. The granulate, dried to a constant weight, is placed in a Turbula Y2A mod. powder mixer and added with magnesium stearate and colloidal silica and mixed fop 20 minutes.

The lubricated granulate is submitted to the compression stage as forward described.

6-d: Preparation of the Three Layers Systems (by Compression)

The granulates obtained according to what formerly reported are loaded in the three loading hoppers of a rotating press suitable to produce three layers tablets (ex. Manesty Layer—Press, Liverpool UK). In particular in the first one the granulate described at the point 6-b is loaded; in the second hopper the granulate according to what is described in the former point 6-a and in the third hopper the granulate described in the point 6-c are loaded. The pressing machine is equipped with circular convex punchs of 12 mm diameter and R=12 mm.

The machine is adjusted for producing three layers systems constituted by a first shape of 90 mg of slow hydration barrier granulate, a second layer of 231 mg containing the active principle (equivalent to 100 mg of ketoprofene) and a third layer of 90 mg of erodible barrier. Working as formerly described, three layers tablets of 411,5 mg average weight each containing 100 mg of active principle are obtained.

6-e: Dissolution Test

To estimate the releasing characteristics of the finished systems the equipment 2, (paddle USP XXII), at 100 r.p.m. is used, using as dissolution fluid 1 liter of simulated intestinal fluid pH=7,5 (according to USP XXII, without enzymes) at 37° C. The active principle release is measured with spectrophotometric determination U.V.: at 262 nm using an automatic system of sampling and reading (Spectracomp 602 by Advanced Products Milano).

The results of the effected tests are reported in the table VI.

TABLE VI

| Time (h) | % released |
|---|---|
| 1 | 0,9 |
| 2 | 2,4 |
| 3 | 7,5 |
| 4 | 12,9 |
| 6 | 23,8 |
| 8 | 42,9 |
| 10 | 72,0 |
| 12 | 90,5 |
| 14 | 100,9 |

It is possible to point out that from the prepared systems it is obtained a range of 3–4 hours during which the drug is practically not released or the release results extremely slowed, and a second phase, clearly different from the former, during which the drug is released at controlled rate in about 14 hours.

Such behaviour completely answers to the invention aims.

Total area 309,8 mm$^2$; exposed area 37,9 mm$^2$; exposed area 12,2%.

To clear up we give hereon a summary table of the total surfaces of the lenticular tablets according to the invention, prepared according to the examples 1–6 before described in detail, and of the exposed surface of the core containing the active principle.

It is clear that the drug release profile and in particular the null or practically null release starting time, are controlled by the percentage of the surface exposed to the physiologic liquids, able to release the active principle. Said profiles are reported in the table 2, FIGS. 4 and 5, for the examples 1 and 2 respectively while they are reported in the table 3, respectively in the FIGS. 6, 7, 8, 9, fop the examples 3, 4, 5, 6.

Summary Table: Core Surface Exposed to the Release

| Three layers system | Total area (mm$^2$) | Exposed area (mm$^2$) | Exposed area (%) |
|---|---|---|---|
| Ex. 1: (Nifedipine 30 mg) | 226,6 | 54,3 | 20,3 |
| Ex. 2: (Nifedipine 30 mg) | 287,3 | 53,9 | 18,7 |
| Ex. 3: (Nicardipine 60 mg) | 253,6 | 62,7 | 24,7 |
| Ex. 4: (Diflunisal 500 mg) | 483,2 | 154,0 | 31,9 |
| Ex. 5: (Diflunisal 500 mg) | 480,2 | 151,0 | 32,0 |
| Ex. 6: (Ketoprofen 100 mg) | 309,8 | 37,9 | 12,2 |

We claim:

1. A controlled release pharmaceutical tablet, having a lenticular form consisting of the 3 following over-imposed layers:

a central layer or core (a) comprising an active principle, 2 external barrier layers (b) and (c) respectively upon and under said core (a) limiting the active principle release, each barrier (b) and (c) comprising a gellable and/or erodible polymeric material, wherein said barrier layers (b) and (c) have the same or different composition and leave exposed only the lateral surface of the core (a), said exposed lateral surface ranging from 5 to 35% of the total tablet surface.

2. The controlled release pharmaceutical tablet according to claim 1, wherein the core (a) additionally contains:

from 1 to 90%, based on the total core weight, of polymeric substances capable of modulating the active principle release, said polymeric substances selected from the group consisting of: crosslinked polivinylpyrrolidone, hydroxypropylmethylcellulose, hydroxypropyl-cellulose, crosslinked sodium carboxymethylcellulose, carboxymethyl starch, acrylic and methacrylic acid polymers and copolymers, polyesters, polyanhydrides copolymers, polymethylvinylether/anhydride, potassium methacrylate-divinylbenzene copolymer, polivinylalcohols, glucan, scleroglucan, mannan, betacyclodextrans, and mixtures thereof;

hydrophilic substances selected from the group consisting of: sorbitol, mannitol, lactose and xilitol, surface active agents and wetting substances; and hydrophobic substances selected from the group consisting of: gliceryl monostearate, hydrogenated castor oil, waxes, mono-, bi- and tri-substituted glycerides.

3. The controlled release therapeutical tablet according to claim 2, wherein the core (a) contains:

from 10 to 45% by weight based on the total core weight of a polymeric substance selected from the group consisting of: hydroxypropylmethylcellulose, crosslinked polyvinylpyrrolidone, sodiumcarboxymethylcellulose and mixtures thereof, a hydrophilic substance consisting of mannitol, and a hydrophobic substance consisting of hydrogenated castor oil.

4. The controlled release pharmaceutical tablet according to claim 1, wherein each of said barrier layers (b) and (c) comprises from 5 to 90% based on the total barrier layer weight of a gellable and/or erodible polymer selected from the group consisting of hydroxypropylmethylcellulose with molecular weight comprised between 1000 and 4,000,000, hydroxypropylcellulose with molecular weight comprised between 2000 and 2,000,000, carboxyvinylpolymers, polyvinylylalcohols, glucans, scleroglucans, mannans, xanthans, alginic acid, polyanhydrides, polyaminoacids, methylvinylethers/maleic anhydride copolymers, carboxymethylcellulose, ethylcellulose, methylcellulose and mixtures thereof; and adjuvants selected from the group consisting of glyceryl monostearate, semisynthetic triglycerides derivatives, semi-synthetic glycerides, hydrogenated castor oil, glycerylpalmitostearate, cetyl alcohol, polyvinylpyrrolidone, glycerol, ethylcellulose, methylcellulose, sodium carboxymethylcellulose, magnesium stearate, stearic acid, talc sodium benzoate, boric acid, polyoxyethyleneglycols, colloidal silica and mixtures thereof.

5. The controlled release pharmaceutical tablet according to claim 4, wherein each of said barrier layers (b) and (c) contains:

from 50 to 90% based on the total barrier layer weight of a gellable and/or erodible polymer consisting of hydroxypropylmethylcellulose having an apparent viscosity comprised between 5 and 100,000 cps, an adjuvant selected from the group consisting of mixtures of hydrogenated castor oil, polivinylpyrrolidone, magnesium stearate, colloidal silica.

6. The controlled release pharmaceutical tablet according to claim 1 further comprising a gastroresistant and enterosoluble film wholly coating said finished three layers tablet, said polymeric film being selected from the group consisting of cellulose acetophtalate, cellulose trimellitate, acrylic and methacrylic polymers and copolymers with different molecular weight and with solubility dependant on different pH values.

* * * * *